(12) United States Patent
Palreddy et al.

(10) Patent No.: US 7,996,082 B2
(45) Date of Patent: *Aug. 9, 2011

(54) METHOD AND DEVICES FOR PERFORMING CARDIAC WAVEFORM APPRAISAL

(75) Inventors: Surekha Palreddy, Maplewood, MN (US); Jay A. Warren, San Juan Capistrano, CA (US); James W. Phillips, Fountain Valley, CA (US)

(73) Assignee: Cameron Health, Inc., San Clemente, CA (US)

( * ) Notice: Subject to any disclaimer, the term of this patent is extended or adjusted under 35 U.S.C. 154(b) by 1005 days.

This patent is subject to a terminal disclaimer.

(21) Appl. No.: 11/781,687

(22) Filed: Jul. 23, 2007

(65) Prior Publication Data

US 2008/0015647 A1    Jan. 17, 2008

Related U.S. Application Data

(62) Division of application No. 10/858,598, filed on Jun. 1, 2004, now Pat. No. 7,248,921.

(60) Provisional application No. 60/475,279, filed on Jun. 2, 2003.

(51) Int. Cl.
*A61N 1/00* (2006.01)

(52) U.S. Cl. .......................................... 607/5

(58) Field of Classification Search .................. 600/323, 600/518, 513; 607/28, 5; 604/66
See application file for complete search history.

(56) References Cited

U.S. PATENT DOCUMENTS

| | | | |
|---|---|---|---|
| 4,589,420 A | 5/1986 | Adams et al. | |
| 5,301,677 A * | 4/1994 | Hsung | 600/518 |
| 6,029,086 A | 2/2000 | Kim et al. | |
| 6,192,273 B1 | 2/2001 | Igel et al. | |
| 6,625,484 B2 | 9/2003 | Kohler et al. | |
| 6,647,292 B1 | 11/2003 | Bardy et al. | |
| 6,721,597 B1 | 4/2004 | Bardy et al. | |
| 6,731,978 B2 | 5/2004 | Olson et al. | |
| 6,892,092 B2 | 5/2005 | Palreddy et al. | |
| 7,330,757 B2 | 2/2008 | Ostroff et al. | |
| 2002/0058878 A1 | 5/2002 | Kohler et al. | |
| 2004/0254613 A1 | 12/2004 | Ostroff et al. | |

FOREIGN PATENT DOCUMENTS

CA    1 138 531    12/1982

(Continued)

OTHER PUBLICATIONS

IPAU Allowance (May 20, 2010), Amendment/Response (Apr. 1, 2010), and IPAU Action (Oct. 12, 2009) for related/family application filed in Australia (AU App. No. 200445030).

(Continued)

*Primary Examiner* — George Manuel
*Assistant Examiner* — Robert N Wieland
(74) *Attorney, Agent, or Firm* — Pramudji Law Group PLLC; Ari Pramudji; Mark Schroeder

(57) ABSTRACT

Implementations of various technologies described herein are directed toward a sensing architecture for use in cardiac rhythm management devices. The sensing architecture may provide a method and means for certifying detected events by the cardiac rhythm management device. Moreover, by exploiting the enhanced capability to accurately identifying only those sensed events that are desirable, and preventing the use of events marked as suspect, the sensing architecture can better discriminate between rhythms appropriate for device therapy and those that are not.

26 Claims, 12 Drawing Sheets

FOREIGN PATENT DOCUMENTS

| | | | |
|---|---|---|---|
| EP | 554208 A2 * | 8/1993 | |
| GB | 2 034 046 A | 5/1980 | |
| WO | 93-20888 A1 | 10/1993 | |
| WO | 00-16852 A1 | 3/2000 | |

OTHER PUBLICATIONS

SIPO Allowance (Aug. 12, 2010), Amendment/Response (Feb. 12, 2010), SIPO Action (Dec. 4, 2009), Amendment/Response (Jul. 20, 2009) and SIPO Action (Mar. 6, 2009) for related/family application filed in China (CN App. No. 2004 80022179.5).

Amendment/Response (Apr. 28, 2010) and EPO Action (Dec. 21, 2009) for related/family application filed in Europe (EP App. No. 04753836.8).

Amendment/Response (Feb. 25, 2010) and JPO Action (Oct. 27, 2009) for related/family application filed in Japan (JP App. No. 2006-515033).

* cited by examiner

METHOD AND DEVICES FOR PERFORMING CARDIAC WAVEFORM APPRAISAL

CROSS-REFERENCE OF RELATED APPLICATIONS

This application is a divisional of U.S. patent application Ser. No. 10/858,598, filed Jun. 1, 2004, titled METHOD AND DEVICES FOR PERFORMING CARDIAC WAVEFORM APPRAISAL, and now U.S. Pat. No. 7,248,921, which claims the benefit of U.S. Provisional Application Ser. No. 60/475,279, filed Jun. 2, 2003, and titled METHOD FOR VALIDATING DETECTION IN SENSING ALGORITHMS. Each of the aforementioned related patent applications is herein incorporated by reference.

BACKGROUND

1. Field

Implementations of various technologies described herein are related to the field of implantable cardiac treatment devices, and more particularly, to methods of electrically sensing cardiac events and confirming the accuracy in detecting a cardiac event prior to determining whether treatment is needed.

2. Description of the Related Art

The following descriptions and examples do not constitute an admission as prior art by virtue of their inclusion within this section.

Implantable cardiac rhythm management devices are an effective treatment in managing irregular cardiac rhythms in particular patients. Implantable cardiac rhythm management devices are capable of recognizing and treating arrhythmias with a variety of therapies. These therapies range from providing anti-bradycardia pacing for treating bradycardia, anti-tachycardia pacing or cardioversion energy for treating ventricular tachycardia, to high energy shock for treating ventricular fibrillation. Frequently, the cardiac rhythm management device delivers these therapies for the treatment of tachyarrhythmias in sequence; starting with anti-tachycardia pacing and then proceeding to low energy shocks, and then, finally, to high energy shocks. Sometimes, however, only one of these therapies is selected depending upon the tachyarrhythmia detected.

To effectively deliver these treatments, cardiac rhythm management devices must first accurately detect and classify an episode. Through accurate determination and quantification of sensed cardiac events, these cardiac rhythm management devices are able to classify the type of arrhythmia that is occurring and assess the appropriate therapy to provide to the heart, if any. A problem arises, however, when the cardiac rhythm management device senses noise, and mistakenly declares an episode. As a result, in particular instances, the cardiac rhythm management device may inappropriately deliver therapy.

Extra-cardiac noise may cause a cardiac rhythm management device to misclassify noise events as a tachyarrhythmia. In illustration, by incorporating skeletal muscle noise artifact, or other noise, into a cardiac rate calculation, the cardiac rhythm management device might inaccurately calculate the ventricular rate as one that is elevated. If the ventricular rate is mistakenly calculated to be elevated over a threshold rate boundary, a frequent determiner of tachyarrhythmias, the cardiac rhythm management device may inappropriately deliver therapy to a patient.

Additionally, problems arise when the cardiac therapy device withholds therapy after mischaracterizing a sensed event. For example, anti-bradycardia devices deliver a pacing pulse based on whether a cardiac event is sensed within a particular time frame. If the sensing architecture fails to sense a cardiac event within a preset time period, the cardiac rhythm management device will deliver a pacing pulse to the heart. This pacing pulse is timed in a preset sequence to induce the patient's heart to contract in a proper rhythm. This therapy, however, may be compromised by having the cardiac rhythm management device sense and characterize an extraneous event as a "true" cardiac event. If the sensing architecture erroneously classifies noise (such as skeletal muscle artifact or other noise) as a "true" cardiac event, then a pacing pulse may be incorrectly withheld. This is particularly problematic when a pacing pulse is required to maintain a physiologically necessary rate of the patient's heart.

Besides being noticeable and sometimes physically painful to the patient, when a cardiac rhythm management device delivers inappropriate treatment, it can be extremely disconcerting to the patient. Moreover, delivery of an inappropriate therapy can intensify the malignancy of the cardiac arrhythmia. Therefore, the accuracy of a sensing architecture is an important factor in ensuring that appropriate therapy is delivered to a patient.

Current implantable cardiac rhythm management devices incorporate a sensing architecture that detects likely cardiac events and renders a decision regardless of the accuracy of those originally detected events. As such, current implantable cardiac rhythm management devices must include painstakingly designed sensing architectures to try and avoid erroneous detections. Prior art devices have been developed with rudimentary systems and methods in an attempt to determine whether noise is present on a sampled cardiac signal. If noise is detected in these devices, the manner in which the cardiac signal is acquired, or the manner in which the device operates in response to the acquired signal, is altered. This reduces the impact of erroneously detecting noise and, therefore, inappropriately triggering or withholding therapy. This methodology, however, leaves the cardiac rhythm management device open to significant sensing drawbacks, one of which is that it continually perturbates the sensing architecture.

Certain prior art implantable cardiac rhythm management devices continuously adjust parameters such as amplifier gain in response to extra-cardiac noise, which allows for the possibility that the sensing architecture may miss cardiac events. When adjusting the gain control to lessen sensitivity by raising the sensing floor to avoid noise, it is possible to miss actual cardiac events especially during polymorphic rhythms including ventricular fibrillation. In particular, the sensing architecture may miss discrete cardiac beats, or otherwise stated, miss true positives. By missing a cardiac event, rhythm and beat sensitivity is diminished.

Other implantable cardiac rhythm management devices in the prior art repeatedly extend a noise window during continuous noise. When these window extensions either reach a specific number, or more commonly reach the end of a predetermined interval, the device reverts to a non-sensing or asynchronous behavior for a limited period of time. This type of reversion behavior can miss a cardiac event, therefore reducing rhythm and beat sensitivity. Additionally, these reversion approaches to noise are generally only useful for continuous noise. Noise is most frequently burst in nature, for which most reversion schemes are not effective. This often results in overdetection and a potential for inappropriate therapy. Prior art cardiac rhythm management devices frequently utilize these methodologies contiguously.

SUMMARY

Implementations of various technologies described herein are directed toward a sensing architecture for use in cardiac rhythm management devices. The sensing architecture provides a method and means for certifying detected events by the cardiac rhythm management device. Moreover, by exploiting the enhanced capability for accurately identifying and using information from only those sensed events that are certified, the sensing architecture can better discriminate between rhythms appropriate for device therapy and those that are not.

Implementations of various technologies described herein are also directed toward a method of signal detection enhancement for a cardiac rhythm device comprising receiving a signal from electrodes implanted for cardiac observation, observing characteristic features of the signal, counting the characteristic features, and comparing the number of characteristic features to a threshold either to certify the signal for use in characterizing a cardiac complex, or to determine the signal is unsuitable for use in characterizing a cardiac complex. In some implementations, the characteristic features may include a number of significant maximum slope points in the sensed signal. In other implementations, the characteristic features may include a number of monotonic segments in the sensed signal, or may include a number of sample groups within the sensed signal that are monotonic. Additional implementations may include systems and devices suited for performing such methods.

The above referenced summary section is provided to introduce a selection of concepts in a simplified form that are further described below in the detailed description section. The summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION

Implementations of various technologies will hereafter be described with reference to the accompanying drawings. It should be understood, however, that the accompanying drawings illustrate only the various implementations described herein and are not meant to limit the scope of various technologies described herein.

DETAILED DESCRIPTION

The discussion below is directed to certain specific implementations. It is to be understood that the discussion below is only for the purpose of enabling a person with ordinary skill in the art to make and use any subject matter defined now or later by the patent "claims" found in any issued patent herein.

Implementations of various technologies are generally related to cardiac rhythm management devices (e.g., an Implantable Cardioverter/Defibrillator (ICD) system) that provide therapy for patients experiencing particular arrhythmias. Implementations of various technologies are directed toward sensing architectures for use in cardiac rhythm management devices. In particular, implementations of various technologies are suited for ICD systems capable of detecting and defibrillating harmful arrhythmias. Although the sensing architecture is intended primarily for use in an implantable medical device that provides defibrillation therapy, various implementations are also applicable to cardiac rhythm management devices directed toward anti-tachyarrhythmia pacing (ATP) therapy, pacing, and other cardiac rhythm devices capable of performing a combination of therapies to treat rhythm disorders, including external devices.

Figure 1A:
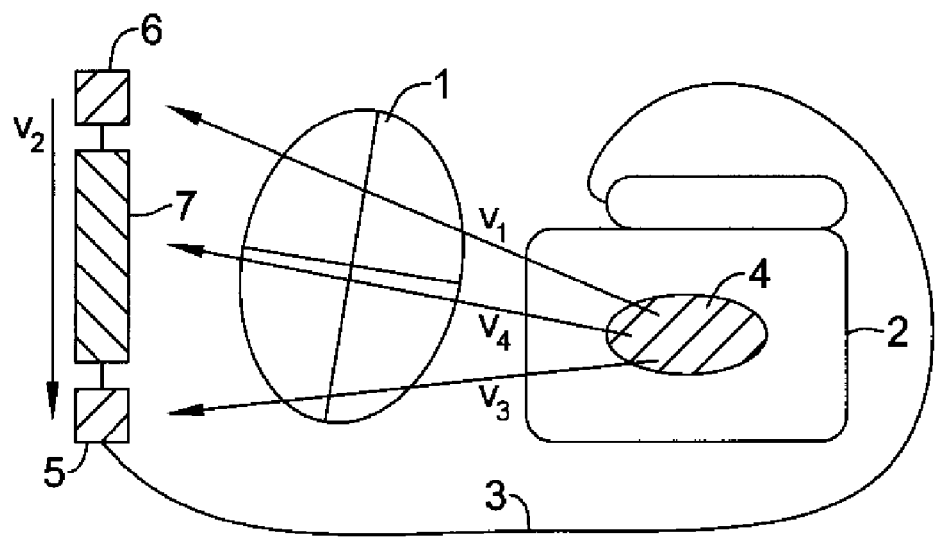
FIGS. 1A-1B illustrate, respectively, representative subcutaneous and intravenous ICD systems in connection with implementations of various technologies described herein.
Figure 1B:
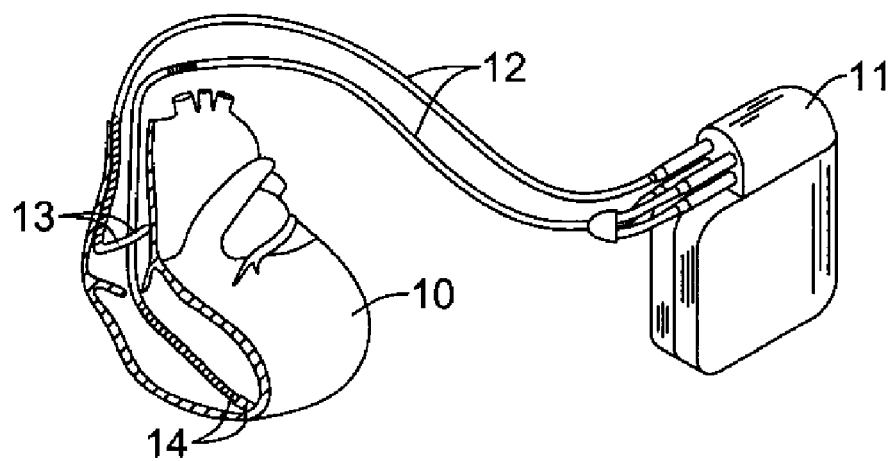

To date, ICD systems have been epicardial systems or transvenous systems implanted generally as shown in FIG. 1B. However, as further explained herein, various implementations are also adapted to function with a subcutaneous ICD system as shown in FIG. 1A.

FIG. 1A illustrates a subcutaneously placed ICD system. In this implementation, the heart 1 is monitored using a canister 2 coupled to a lead system 3. The canister 2 may include an electrode 4 thereon, while the lead system 3 connects to sensing electrodes 5, 6, and a coil electrode 7 that may serve as a shock or stimulus delivery electrode as well as a sensing electrode. The various electrodes define a number of sensing vectors V1, V2, V3, V4. It can be seen that each vector provides a different vector "view" of the heart's 1 electrical activity. The system may be implanted subcutaneously as illustrated, for example, in U.S. Pat. Nos. 6,647,292 and 6,721,597, the disclosures of which are both incorporated herein by reference. By subcutaneous placement, it is meant that electrode placement does not require insertion of an electrode into a heart chamber, the heart muscle, or the patient's vasculature.

FIG. 1B illustrates a transvenous ICD system. The heart 10 is monitored and treated by a system including a canister 11 coupled to a lead system 12 including atrial electrodes 13 and ventricular electrodes 14. A number of configurations for the electrodes may be used, including placement within the heart, adherence to the heart, or disposition within the patient's vasculature. For example, Olson et al., in U.S. Pat. No. 6,731, 978, illustrate electrodes disposed in each chamber of the heart for sensing, as well as shocking electrodes in addition to the sensing electrodes.

Various implementations may also be embodied by operational circuitry including select electrical components provided within the canister 2 (FIG. 1A) or canister 11 (FIG. 1B). In such implementations, the operational circuitry may be configured to enable the methods to be performed. In some similar implementations, various technologies described herein may be embodied in readable instruction sets such as a program encoded in machine or controller readable media, wherein the readable instruction sets are provided to enable the operational circuitry to perform the analysis discussed in the above referenced implementations. Further implementations may include a controller or microcontroller adapted to read and execute the above methods.

Figure 2:
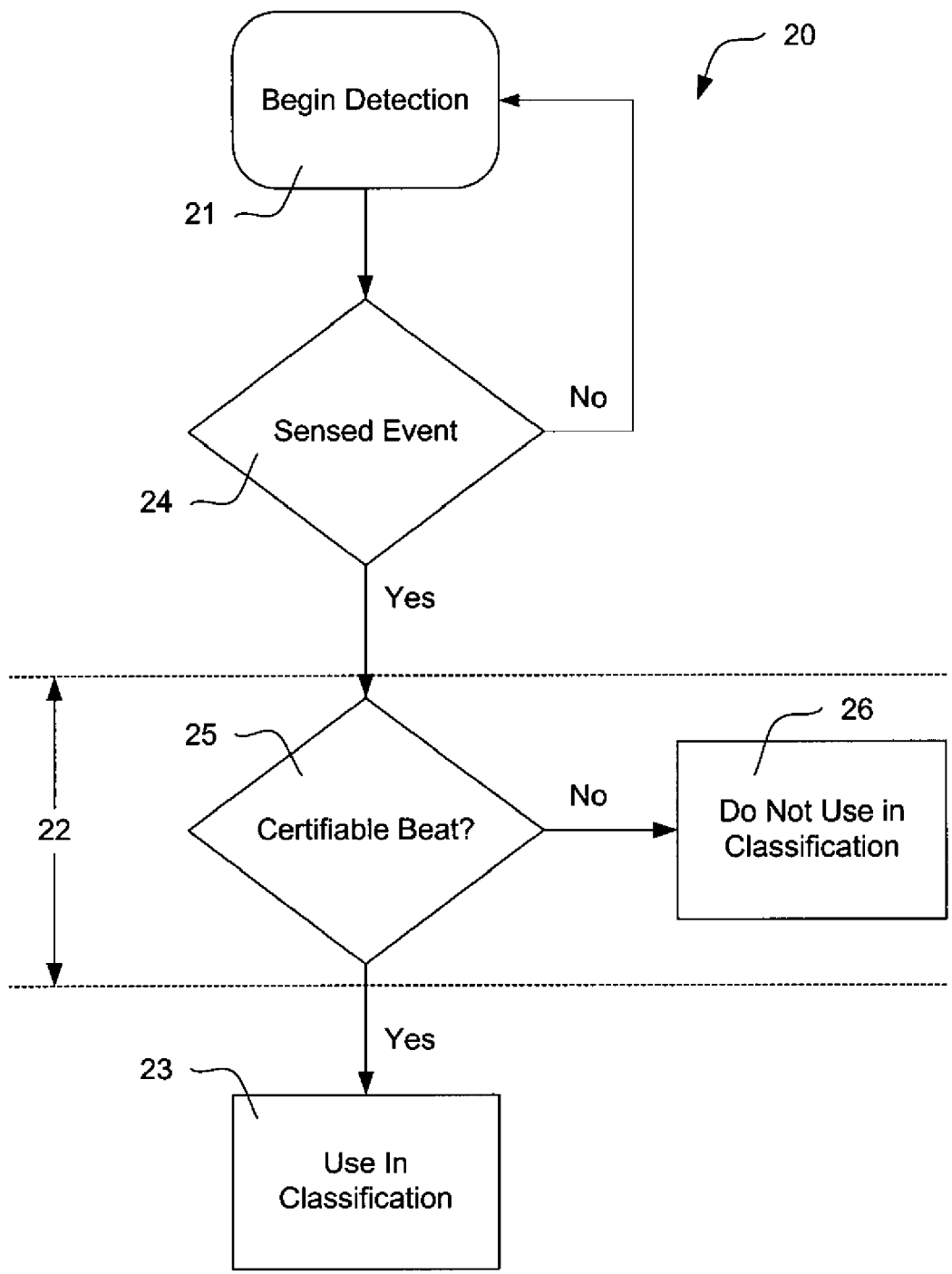
FIG. 2 illustrates a block diagram of a sensing architecture in accordance with implementations of various technologies described herein.

FIG. 2 illustrates a sensing architecture 20 in accordance with implementations of various technologies described herein. The sensing architecture 20 is separated into three distinct and autonomous phases. The three phases are (1) the detection phase 21, (2) the waveform appraisal phase 22 and (3) the classification phase 23. Decisions are made in each of the three phases. Moreover, decisions made in each phase may affect the decision-making process in subsequent phases. However, it is not necessarily the case that decisions made in an individual phase will affect the decision-making process in preceding phases. In illustration, a decision made in the waveform appraisal phase 22 may affect the decision-making process in the classification phase 23, but it may have no effect on the detection phase 21, or in any future decisions made in the detection phase 21.

The first phase of the sensing architecture 20 is the detection phase 21. Within the detection phase 21 of the sensing architecture 20, data is collected by a cardiac rhythm management device. The manner in which the data is collected and the type of data collected is dependent on the cardiac rhythm management device being used. Moreover, the cardiac rhythm management device can be programmed to, or may automatically adapt to, optimally detect a particular form of data which is sought by the cardiac rhythm management device. In a subcutaneous ICD system, subcutaneous electrodes are used to detect cardiac signals emitted from the patient's heart.

Once the raw detected signal data is received by the cardiac rhythm management device, the detected data is then preprocessed, if required or desired. Preprocessing steps may include smoothing of the detected data, differentiation, filtering and other preprocessing methodologies known in the art. Finally, the detected data, whether preprocessed or raw, is initially classified as being either an event or not an event— indicated in the block diagram at 24. More specifically, a determination is made that an event was detected by the sensing architecture 20. An illustrative determination that an event was detected may include, for example, a determination that a signal has been received having at least a certain amplitude likely indicating an R-wave from a cardiac complex or noise. The result is that the detection phase 21 provides a sensed event to the waveform appraisal phase 22.

Following the detection phase 21 of the sensing architecture 20, sensed events are appraised in the second phase, the waveform appraisal phase 22. In the illustrative implementation, the waveform appraisal phase 22 is a separate and independent phase in the sensing architecture 20. It is within the waveform appraisal phase 22 where an analysis is performed on the sensed event 24 recognized in the detection phase 21 of the sensing architecture 20. In the waveform appraisal phase 22, an operation is performed on the sensed event. More specifically, the appraisal operator 25 evaluates and certifies that what is sensed during the detection phase 21 is a high quality sensed event. A high quality sensed event is a sensed event that can be used in classifying a cardiac rhythm, such as a sensed event that closely represents a cardiac "beat" without excessive noise. In contrast, a low quality event may be a noise signal that does not represent the desired cardiac signal, or may represent a sensed cardiac beat but the beat is superimposed with a noise artifact sufficient to render the sensed event unsuitable for classification.

In one implementation, the sensed event being certified in the waveform appraisal phase 22 is the detection of a cardiac ventricular depolarization. In the art, a cardiac ventricular depolarization is often referred to as a QRS complex or R-wave. In this implementation, the waveform appraisal phase 22 evaluates and certifies that the sensed event is a high quality R-wave that can be used for further decision making. In some implementations, the events being certified may be the detection of a P-wave (cardiac atrial depolarization), T-wave (cardiac ventricular repolarization), a pacing artifact, or any other sensed signal that may be utilized within a rhythm classification architecture. Various technologies described herein may also evaluate whether the sensed event was not an R-wave, P-wave, T-wave, pacing artifact, or any other sensed signal that could be misidentified as the sensed event of particular interest.

In particularly noisy conditions, certain noise may appear as a cardiac event, and thus be mistakenly sensed as such. Examples of noise that may create a low quality electrocardiogram signal include extra-cardiac (skeletal) muscle artifact, 50/60 Hertz interference, electromagnetic interference, electrocautery, or any other passing or intermittent electrical occurrence.

Assuming that the detection phase 21 does sense noise as an event, this sensed event is then processed through the waveform appraisal phase 22 so that the sensed event may be certified. For the illustrative implementation, at least some, but preferably all sensed events are processed through the waveform appraisal phase 22. In the waveform appraisal phase 22, the appraisal operator 25 examines the sensed event through various methods and procedures (described below). In this example, noise may diminish the quality of the sensed event. Thus, the sensed event would be determined by the appraisal operator 25 to be something other than a certifiable event. A non-certifiable event is one that is "suspect". Once the appraisal operator 25 has determined that the sensed event cannot be a certifiable event, the appraisal operator 25 further makes the determination to refrain from presenting the suspect event to the third phase of the sensing architecture 20, the classification phase 23. Specifically, the appraisal operator 25 prevents information from suspect event 26 from proceeding any further in the decision making process of the sensing architecture 20. As such, the waveform appraisal phase 25 greatly reduces the likelihood that suspect events will inappropriately direct treatment.

In further illustration, the appraisal operator 25 also confirms accurately sensed events. When an accurately sensed event is presented to the appraisal operator 25 of the sensing architecture 20, it will be certified. After the appraisal operator 25 has confirmed that the sensed event is certifiable, the appraisal operator 25 then presents the sensed event to the classification phase 23 for its consideration. Thus, again, only sensed events that have been processed through the waveform appraisal phase 22 will be presented to the classification phase 23 of the sensing architecture 20. All suspect events are prevented 26 by the appraisal operator 25 from being available to the classification phase 23.

The third and final phase of the sensing architecture 20 is the classification phase 23. The classification phase 23 receives data corresponding to events certified by the appraisal operator 25 and performs certain mathematical operations to this certified data. Through these mathematical operations, the classification phase 23 examines attributes such as rate, template comparisons and morphological characteristics, among others. Some illustrative classification phase 23 operations are further discussed in U.S. patent application Ser. No. 10/856,084 titled METHOD FOR DISCRIMINATING BETWEEN VENTRICULAR AND SUPRAVENTRICULAR ARRHYTHMIAS, filed May 27, 2004, now U.S. Pat. No. 7,330,757, and the disclosure of which is incorporated herein by reference. Any other suitable classification or analytical methods may also be used, as desired. These analyses aid the sensing architecture 20 in determining whether the certified events are associated with a particular class of rhythms. The classification phase 23 preferably accumulates a sufficient amount of data to render a determination which directs the cardiac rhythm management device to either withhold or deliver therapy to a patient.

The incorporation of a waveform appraisal phase 22 into a sensing architecture 20 enables various technologies described herein to possess enhanced positive predictivity values. The mathematical formula for positive predictivity is as follows:

Positive Predictivity=(True Positives)/(True Positives+False Positives).

In several illustrative implementations, only certified events, and therefore only the highest quality, accurate and representative data, are designed to be sent to the classification phase 23 for evaluation. As such, even legitimate cardiac signals possessing poor quality may not be sent to the classification phase 23 for evaluation. The waveform appraisal phase 22, therefore, is designed to eliminate the preponderance of false positives from consideration by the classification phase. By reducing the number of false positives observed in a classification scheme, the positive predictivity increases and the system benefits from the reduction in inappropriate therapies delivered to a patient.

This heightened positive predictivity is directly observable in counting schemes used within the classification phase 23 employed by cardiac rhythm management devices. For example, the sensing architecture 20 may utilize an X out of Y parameter requiring the classification of eighteen malignant cardiac events out of twenty-four total detected and certified events to declare an episode. Various implementations can utilize this classic X out of Y filter; however, the Y input may only comprise those events that have been certified. Suspect events, which will include the preponderance of false positives, will have been rejected by the appraisal operator 25 and would not be included in the Y input. Similarly, the X input comprises only those events that are appraised as being certified events through the waveform appraisal phase 22 and classified as dysrhythmic events through the classification phase 23. Thus, a preponderance of false positives are removed by various technologies described herein, dramatically improving the system's positive predictivity.

In contrast, the inclusion of false positive events in the X out of Y filter will result in the reduction of positive predictivity. Therefore, in systems without a waveform appraisal phase 22, the positive predictivity of the counting scheme may be compromised during low quality electrocardiograms. If the positive predictivity is compromised, this may decreases the system's ability to accurately and reliably direct therapy to a patient.

Figure 3:
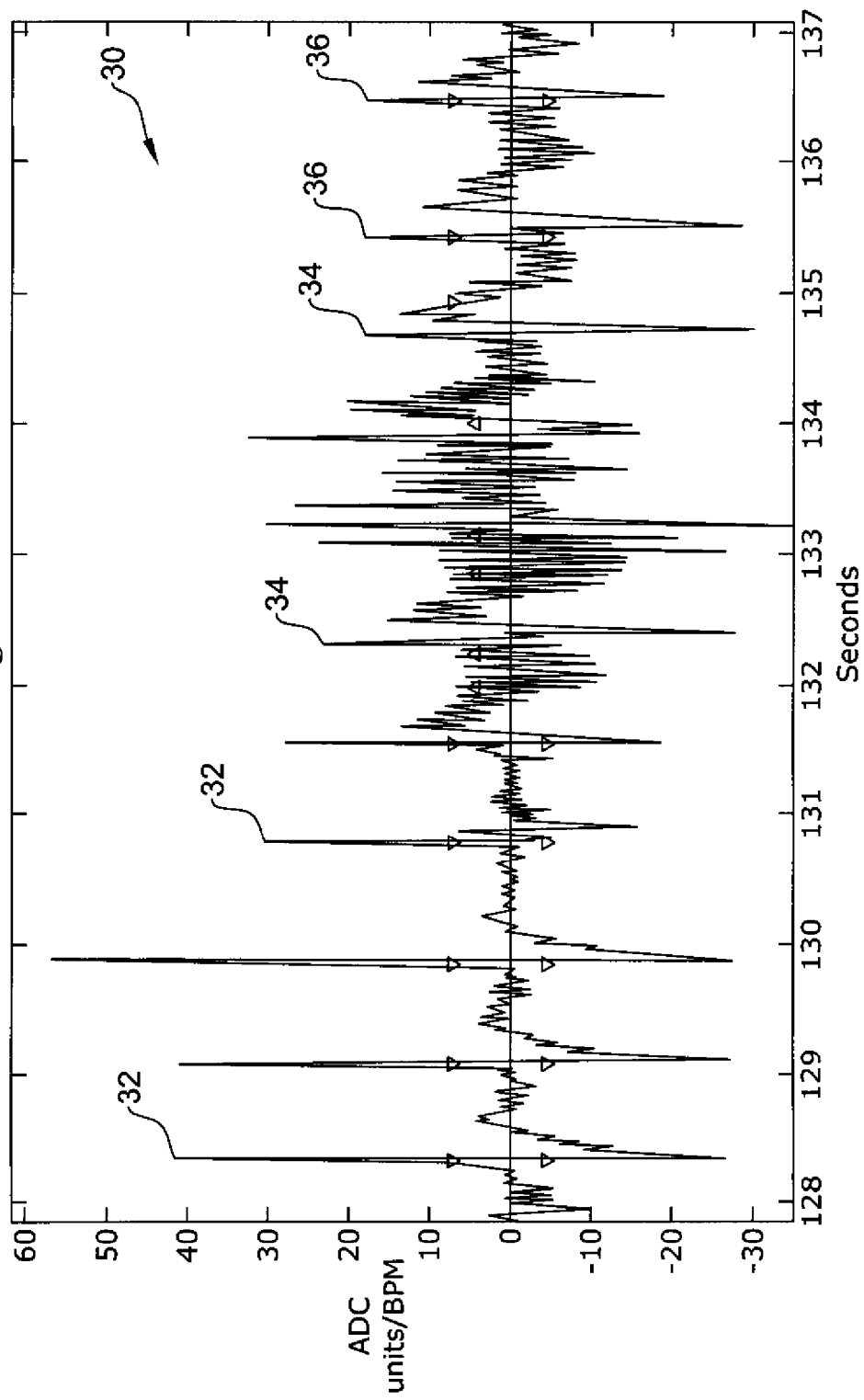
FIG. 3 shows an electrocardiogram having a plurality of certified cardiac complexes used in classification and a plurality of cardiac complexes being marked suspect by the sensing architecture and not used in classification in accordance with implementations of various technologies described herein.

FIG. 3 shows an approximately nine second segment of a patient's electrocardiogram 30 that is of low quality. Referring both to FIGS. 2 and 3, the electrocardiogram in FIG. 3 was processed through the sensing architecture 20; including the waveform appraisal phase 22 of the illustrative implementation. The electrocardiogram 30 shows seven certified events (depicted by the symbol of an inverted triangle) and ten suspect events that were attributed as possessing low quality (depicted by the symbol of a dotted upright triangle). In this particular example, the low quality of the electrocardiogram is attributable to muscle artifact noise.

The first five sensed events 32 in the electrocardiogram were sensed by the detection phase 21, certified through the waveform appraisal phase 22, and presented to the classification phase 23 of the sensing architecture 20 as true cardiac complexes. In contrast, the ten subsequently following sensed events 34 in time were sensed by the detection phase 21, and evaluated and rejected through the waveform appraisal phase 22 as being suspect. Thus, these ten suspect events were not presented to the classification phase 23—as noted illustratively by the placement of a solid dot in an upright triangle. The last two sensed events 36 in time in the electrocardiogram, however, are depicted as being sensed and certified, and were presented to the classification phase 23.

If the overall system makes use of a counter or register to determine when to provide therapy to a patient, the occurrence of suspect events 34-34 need not necessarily reset or undermine the counting scheme to any great extent. In the illustrative example, counting during a low-quality signal is suspended during the occurrence of one, or a series of suspect events—such as those sensed events 34 graphically illustrated in FIG. 3. Implementations of the classification phase 23 of various technologies described herein could suspend the count through the low quality signal detection, and again continue the count where it left off following the passage of the low quality signal detection. Thus, in the above described example, the classification phase 23 would detect the non-continuity of the stream of sensed data, but could still attribute the first certified event following the interruption, the count of eleven and not one. This feature permits the sensing architecture 20 to greatly reduce any delay in detection. More specifically, the counting requirement could be fulfilled more quickly by the ability of various technologies described herein to hold a count as non-certifiable (suspect) events are rejected by the waveform appraisal phase 22, and therefore, would be quicker to declare an episode than a prior art device that must restart the count following the detection of noise. Thus, various technologies described herein are capable of swift and accurate episode detection, which significantly increases the success of therapy delivered to a patient.

Certain implementations of various technologies described herein and counting operations may also limit the ability to suspend a count. For example, it would be less desirable to have a counting operation, requiring a preset number of events before declaring an episode, be one event shy of the required number, experience a considerable low-quality signal detection period, and then declare an episode on the first certified event following the low-quality signal detection. In this last example, various technologies described herein may hold the count out longer to assure that the most recently sensed events are part of the trend observed prior to the low-quality signal detection. Similarly, if a lengthy low-quality signal is observed by some implementations (one that far outnumbers the previously certified events) or the continuity of the sensed signal is extremely poor, those implementations could also restart a count to assure that the declaration is accurate.

Figure 4:
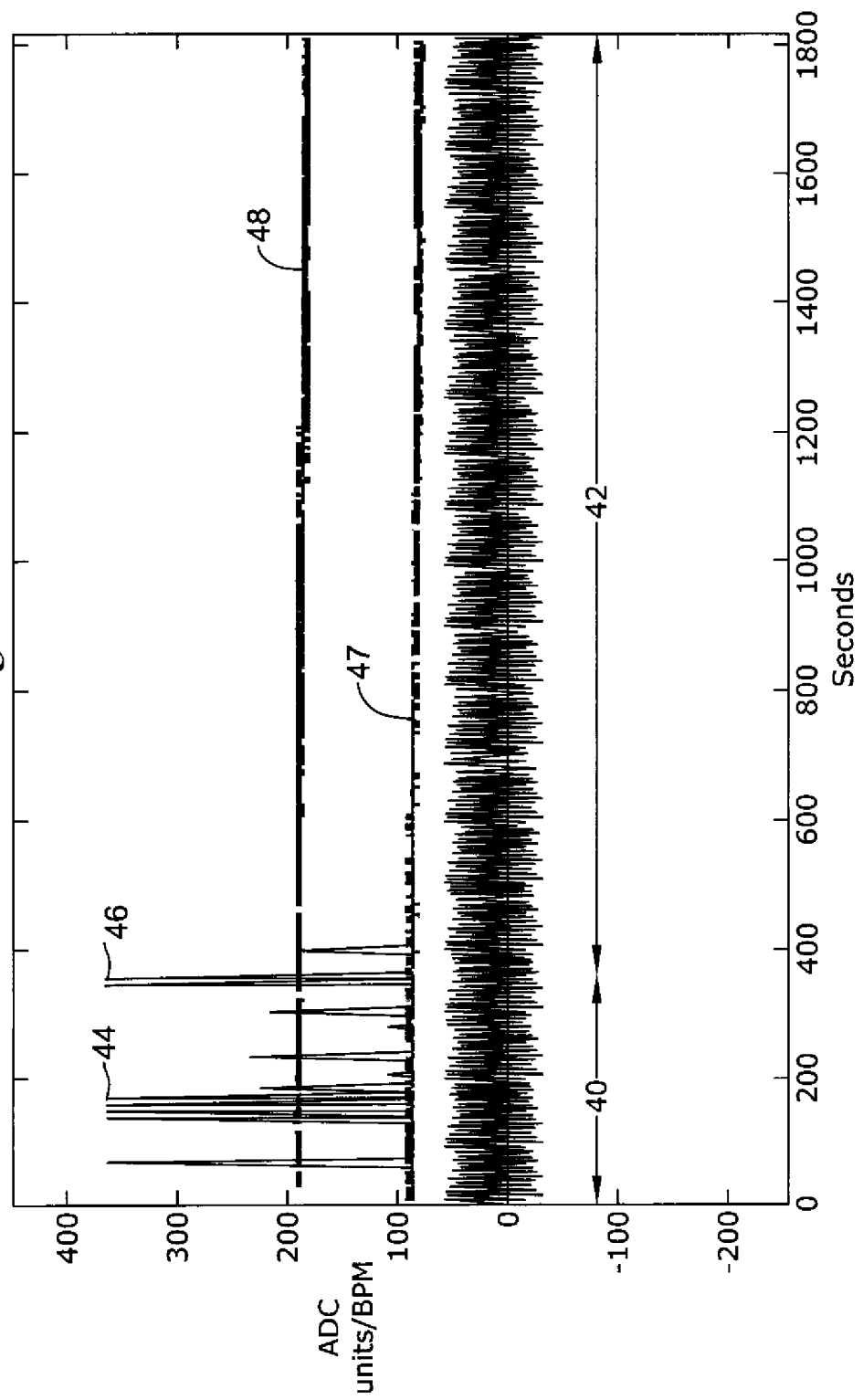
FIG. 4 shows an electrocardiogram sample having no waveform appraisal phase implemented by the sensing architecture in accordance with implementations of various technologies described herein.
Figure 5:
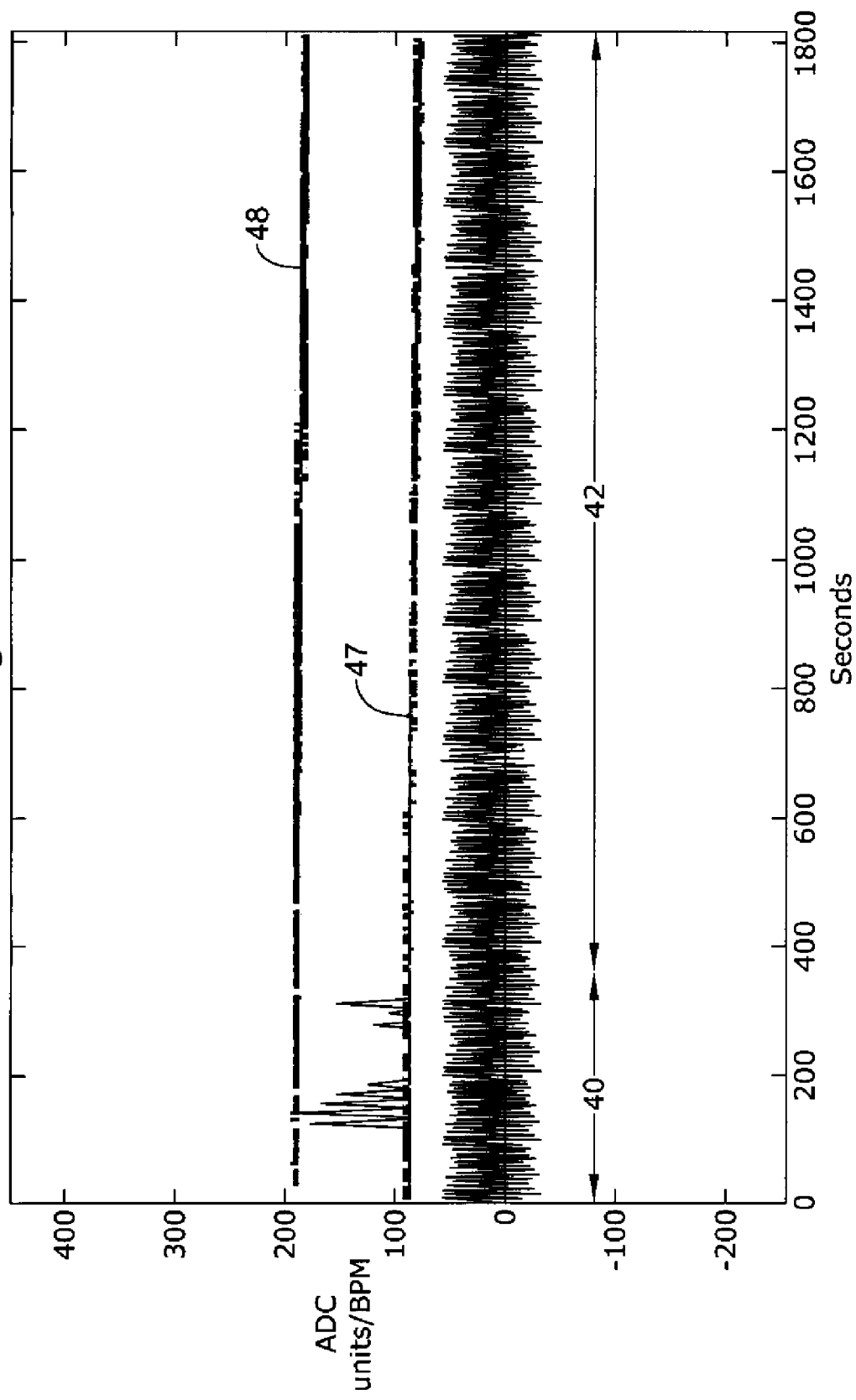
FIG. 5 shows the same electrocardiogram sample as that depicted in FIG. 3, but with the waveform appraisal phase implemented in accordance with implementations of various technologies described herein.

FIGS. 4 and 5 show how the application of various implementations can enhance ICD operation in directing therapy to a patient. The rate threshold for arrhythmia declaration in both FIGS. 4 and 5 is approximately 180 BPM, and is depicted as a solid line 48. The running average cardiac rate is depicted generally as line 47.

The electrocardiogram in FIG. 4 illustrates a scenario where the calculated rate is the only determinative factor in deciding whether to apply or withhold therapy. Therefore, the analytical method applied to the electrocardiogram in FIG. 4 does not include a waveform appraisal phase. In the electrocardiogram of FIG. 4, a normal sinus rhythm interspersed with low quality cardiac events is depicted as segment 40, and a high quality segment of normal sinus rhythm is shown as segment 42.

The upward excursions of the running cardiac rate 47 during segment 40 are caused by the inappropriate counting of low-quality events. As a result of this inappropriate rate counting, the patient would have been delivered at least one inappropriate shock, because the only determinative factor for therapy is rate. The points in the electrocardiogram where an event is declared using a prior art algorithm is shown as lines 44 and 46.

The electrocardiogram in FIG. 5 illustrates a scenario where a sensing architecture such as sensing architecture 20 in FIG. 2 is used, including a waveform appraisal phase 22, as discussed above with reference to FIG. 2. The inclusion of the waveform appraisal phase 22 greatly reduces the instances of inappropriate rate counting, and, therefore, inappropriate shocks, such as the ones declared in FIG. 4. When the illustrative sensing architecture 20 evaluates the same electrocardiogram signal as FIG. 4, it rejects the non-certifiable events as suspect. After the waveform appraisal phase 22 rejects the suspect events, it is observed that the illustrative implementation does not include those suspect events in calculating the running average cardiac rate, and therefore does not deliver therapy. Specifically, when the appraisal operator 20 is presented with the low-quality segment 40, the waveform appraisal phase 22 evaluates the low-quality segment 40, and finds it to be of insufficient quality to use for declaring an event. Thus, in striking comparison to an industry standard sensing architecture as used for the evaluation shown in FIG. 4, the illustrative implementation does not deliver therapy based on the low-quality signals observed in segment 40.

In one implementation, whether a cardiac event is accurately detected by the detection phase 21 of the sensing architecture 20, the detection phase 21 is not adjusted by the waveform appraisal phase's determinations. The detection phase 21 continues to operate independently of the remaining portions of the sensing architecture 20. Thus, although the waveform appraisal phase 22 may be evaluating detected events as suspect beats, the detection phase 21 of the sensing architecture 20 continues to sense such events in its customary manner. In another implementation, the detection phase 21 may adjust its sensing parameters to compensate for the frequency and number of mischaracterized, and therefore, suspect events.

Although various technologies described herein have been described with relation to an ICD, a pacing device, such as a pacemaker, may utilize these various technologies when in an ATP state. Thus, when a pacemaker is pacing a heart out of a tachyarrhythmia, the pacemaker may utilize the multi-phase sensing architecture of various technologies described herein to certify whether sensed events have high quality or whether they are of low quality such that they may cause a mischaracterized detection. Additionally, there are other cardiac rhythm management devices that may have applicable states where the sensing architecture is particularly suited and beneficial.

Referring again to FIG. 2, the sensing architecture 20 may be capable of implementing several appraisal operators 25, and mechanisms necessary for the performance of the waveform appraisal phase 22. As described above, the events sensed are highly dependent on the type of cardiac rhythm management device used. Likewise, the appraisal operator 25, and the mechanics behinds its operation, is highly dependent on both the cardiac rhythm management device used and the type of events sensed and requiring certification. Various technologies described herein, therefore, are not limited in terms of the particular mechanics used during the waveform appraisal phase of the sensing architecture 20. The following descriptions are to illustrate an exemplary mode or configuration chosen from numerous plausible examples.

Figure 6:
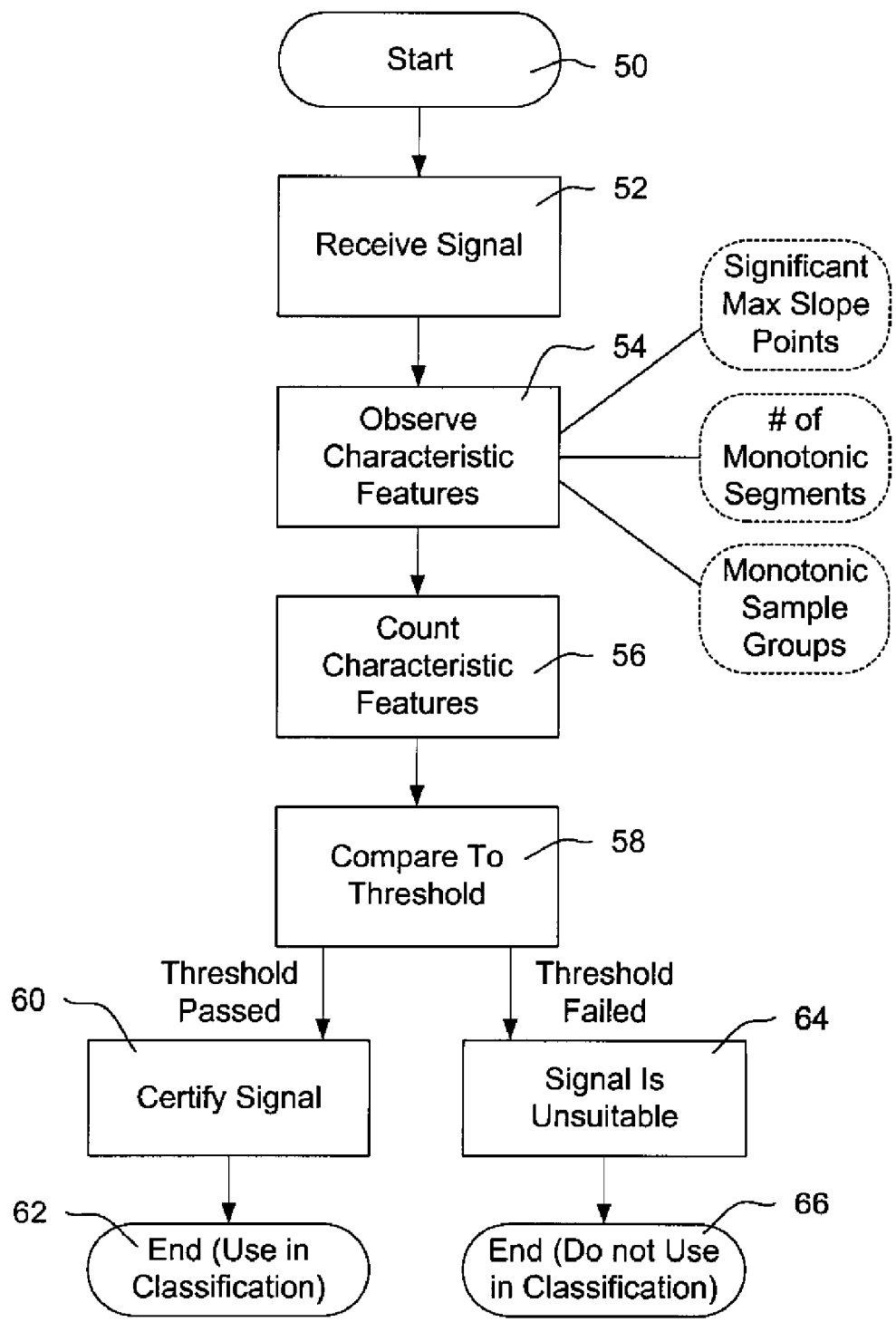
FIG. 6 shows a block diagram illustrating the steps for waveform appraisal in accordance with one implementation of various technologies described herein.

FIG. 6 shows a block diagram illustrating the steps employed in some implementations of various technologies described herein for waveform appraisal. From a start block 50, the waveform appraisal is triggered when an event is sensed, as noted at 52. Next, characteristic features of the sensed event are observed, as shown at 54. As noted, the "characteristic features" may take many forms. In one implementation, the characteristic features concern the shape of the sensed event. Some characteristic features that relate to the event's shape include the inclusion of monotonic segments, monotonic sample groups, or significant maximum slope points (example methods incorporating each are shown, respectively, in FIGS. 7, 8, and 12). Those skilled in the art will recognize that many of the characteristic features provided have suitable alternatives that may be utilized.

The waveform appraisal method in FIG. 6 continues with the step of counting the characteristic features, as shown at 56. The number of characteristic features is then compared to a threshold, as noted at 58. If the threshold is met, the event is certified as shown at 60, and the waveform appraisal is complete 62. The system then submits the certified event to the classification phase for further analysis. If the threshold is not met, the event is found to be a suspect event that is unsuitable for further analysis, as shown at 64. Then, the system is directed to return to the event sensing module or step until a next event is sensed, as shown at 66.

Figure 7:
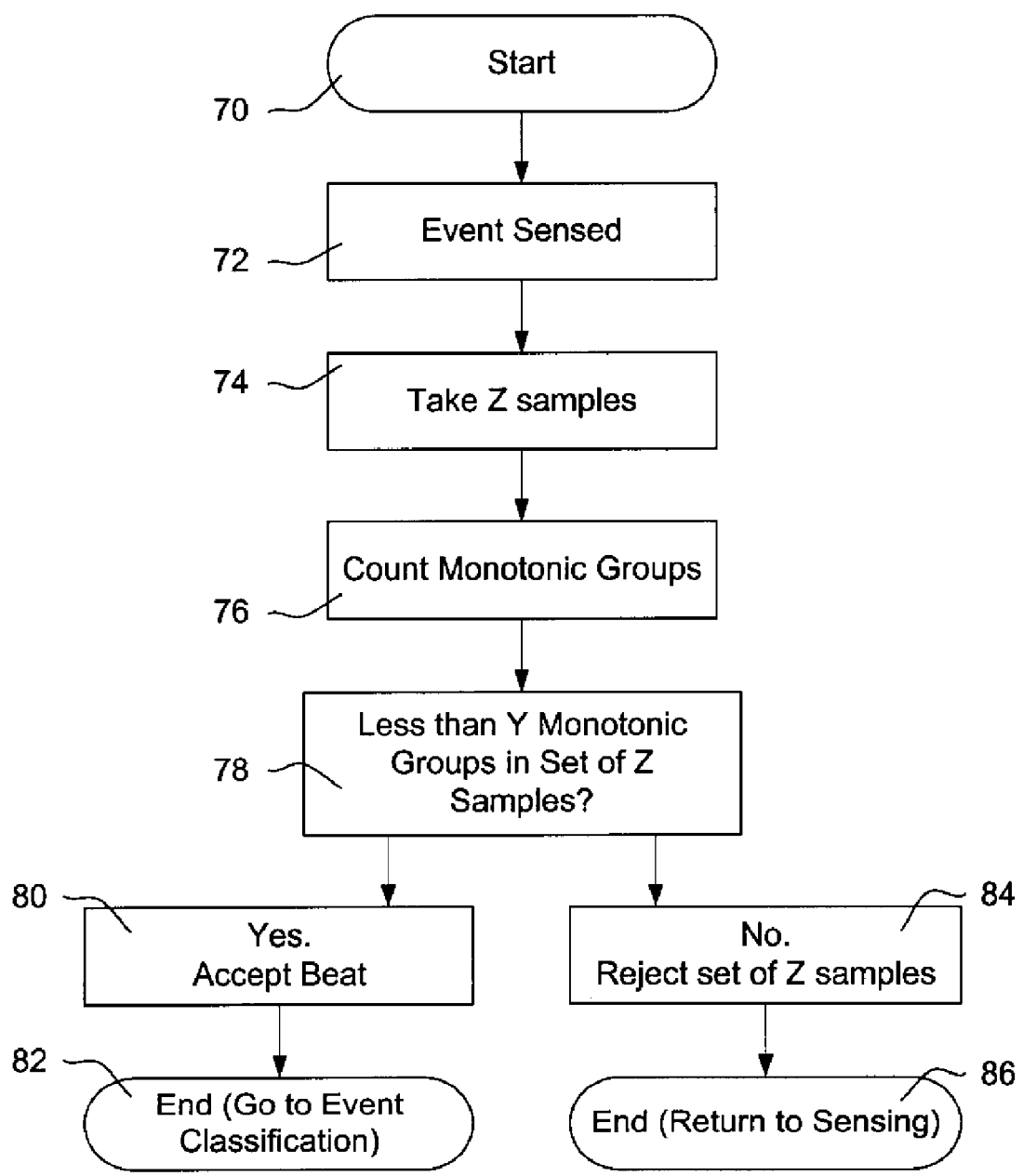
FIG. 7 shows a block diagram illustrating the steps employed for waveform appraisal in accordance with another implementation of various technologies described herein.

FIG. 7 shows a block diagram illustrating the steps employed in another implementation of various technologies described herein for waveform appraisal. From a start block 70, the system senses an event 72. Once the event is sensed 72, the system then implements the waveform appraisal phase, including at least some of steps 74-86. First, a collection of Z samples is taken from the sensed event, as shown at 74. This collection of Z samples is analyzed to count the monotonic groups therein, as noted at 76.

The step of counting monotonic groups 76 may be performed, for example, by comparing each successive sample to its predecessor. First a value for a group counter (typically stored in a counter, register or other memory location) is set to zero. Starting with a first sample, the next sample is compared. If the second sample has a value that is greater than the first sample, a direction register can be set to indicate that the samples are increasing in amplitude with time; alternatively, if the second sample has a value that is less than the first sample, the direction register may be set to indicate that the samples are decreasing. If the second sample has the same amplitude as the first sample, then the direction register may be left at its previous value (which is irrelevant until set). If desired, there may be a minimum change in amplitude required to cause a change in the direction register. Each successive sample is then compared in turn. Whenever the direction register is set to a new value, indicating a change in direction of sensed amplitude change over time, the group counter is incremented to indicate that a new monotonic segment has started.

After the step of counting monotonic groups shown at 76, the number of monotonic groups is compared to a threshold Y, as noted at 78. If there are less than Y monotonic groups in the Z samples, this indicates a high quality sensed event. A YES result 80 calls for certifying the event, and the system goes to an end 82 that directs the certified event to the classification phase. If a NO result 84 occurs, the system rejects the set of Z samples as a suspect event, discarding the samples from memory, and returns to the sensing step as shown at 86.

Figure 8:
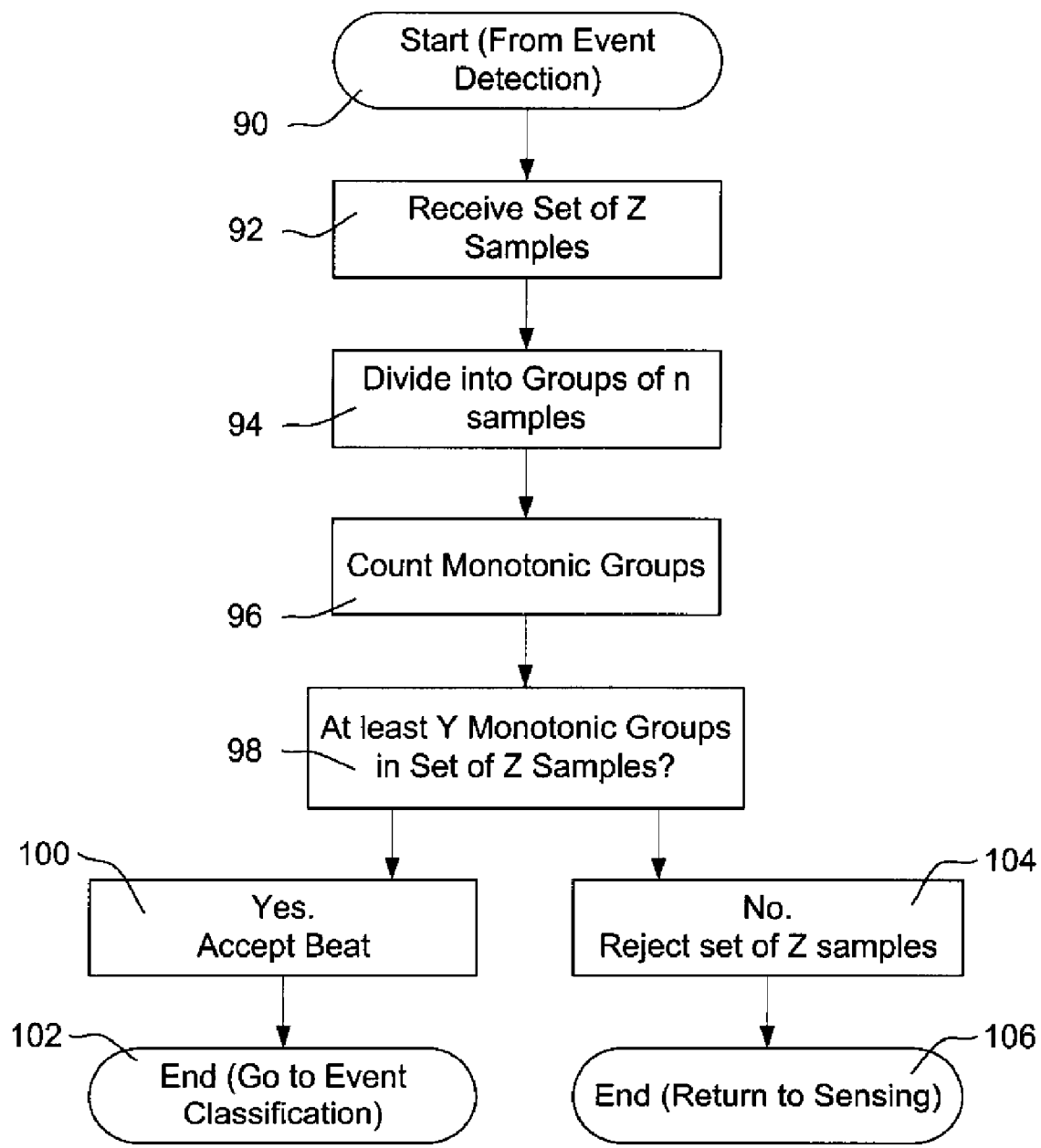
FIG. 8 shows a block diagram illustrating the steps employed for waveform appraisal in accordance with yet another implementation of various technologies described herein.

FIG. 8 is a block diagram of another illustrative implementation of an appraisal system 80 including a waveform appraisal phase. The system begins at start block 90 by the system detecting an event. This illustrative implementation is adapted to work with a sensing architecture that operates in terms of blocks of samples that are received and then sent forward in the analysis structure. As shown at step 92, a set of Z samples are received by the system. The Z samples are then divided into groups of n samples at shown at 94. Each group of samples is evaluated to determine whether it is monotonic or not, and these groups are counted as shown at 96. The system next checks whether at least a threshold value, Y, of the groups are monotonic, as shown at 98. For example, given thirty-two samples, the system may divide the set into eight groups of four samples and determine how many of the groups are monotonic. For such an example, a value of Y=5 could be used, such that five or more of the groups of samples would have to be monotonic to indicate a certified event.

If there are at least Y monotonic groups, the event is certified as a high-quality sensed event, as shown at 100. The waveform appraisal phase then ends and the system directs the certified event to the classification phase, as shown at 102. Otherwise, if there are less than Y monotonic groups in the set of Z samples, the method rejects the set of samples as a suspect event, as shown at 104, and returns to the sensing block as shown at 106.

Figure 9A:
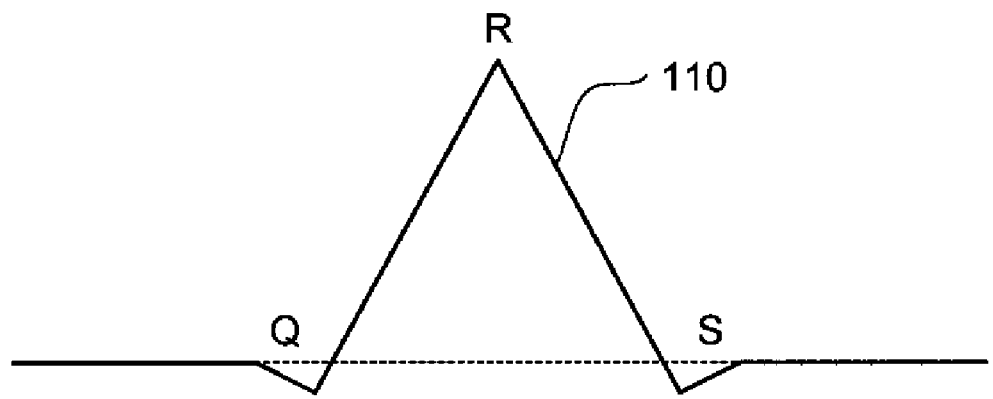
FIGS. 9A-9B illustrate, graphically, operation of the waveform appraisal methods of FIGS. 7 and 8 on a clean QRS signal in accordance with implementations of various technologies described herein.
Figure 9B:
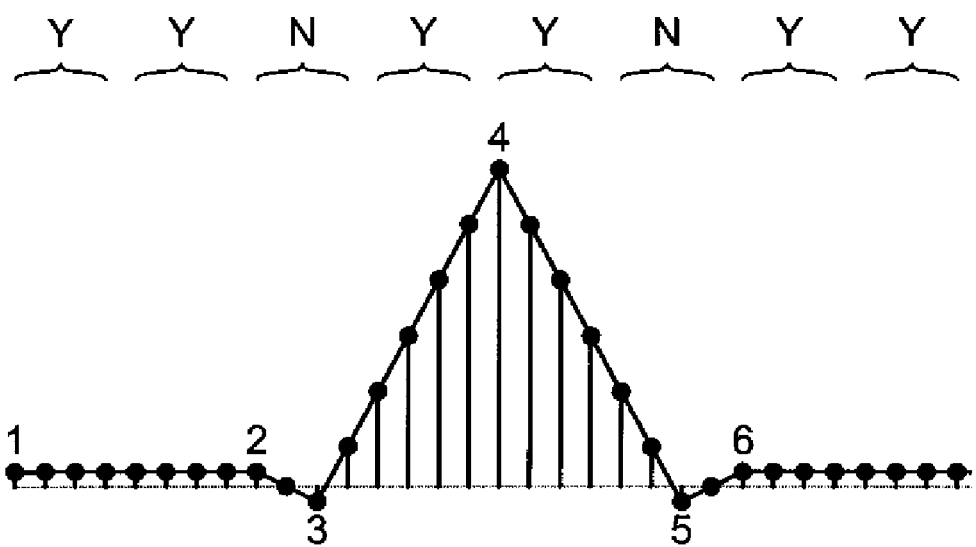

FIGS. 9A-9B show operation of an illustrative waveform appraisal system on a sensed event. The sensed event 110, as shown in its continuous time analog representation in FIG. 9A, is rather idealized and includes only that portion of the cardiac signal including the QRS complex. The T wave, in particular, has been excluded by keeping the time window of sensing narrow. For example, the time window of sensing may be less than one second, less than six-hundred milliseconds, or in the range of about fifty to two-hundred-fifty milliseconds. FIG. 9B illustrates a sampled, discrete time representation of the sensed event 110, with the signal including thirty-two samples. The representation of FIG. 9B, as can be appreciated by looking at FIG. 9A, is a temporally ordered set of samples. The numbers illustrate the number of monotonic segments and when they start by a method similar to the method of FIG. 7. The brackets with Y and N letters placed above illustrate whether grouped samples are monotonic by the method of FIG. 8, with the thirty-two samples placed in groups of four.

As can be seen, the event in FIG. 9B includes six monotonic segments as counted in the manner illustrated in FIG. 7. If a further refinement is included where a segment illustrating no change is not considered a separate monotonic segment, segments 1-2 and 5-6 would each count as a single monotonic segment such that the beat would have only four monotonic segments. If a maximum number of segments is set at six, then the sensed event 110 of FIGS. 9A-9B would be certified.

For the method of FIG. 8, the results of the group checks yields six monotonic groups and two groups that are not monotonic. If a threshold of ⅝ groups being monotonic is used, then the sensed event 110 of FIGS. 9A-9B would be certified.

Figure 10A:
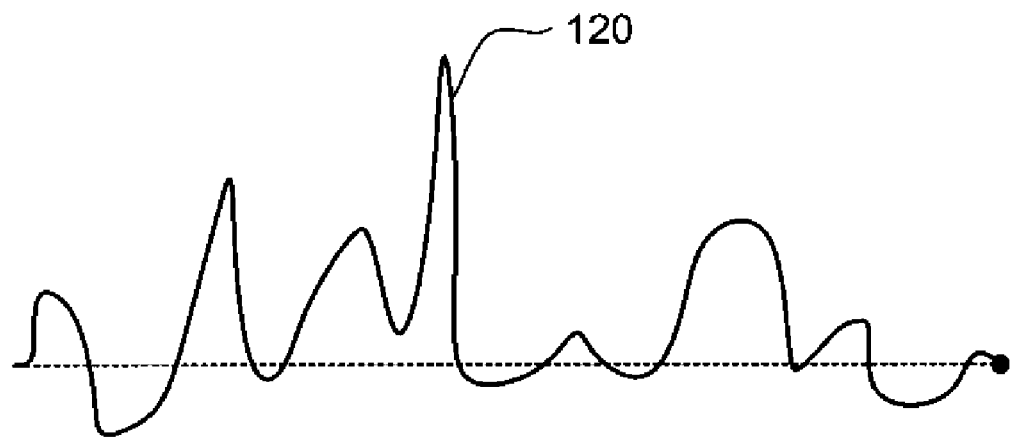
FIGS. 10A-10B illustrate, graphically, operation of the waveform appraisal methods of FIGS. 7 and 8 on a noisy signal that is not suitable for beat classification in accordance with implementations of various technologies described herein.
Figure 10B:
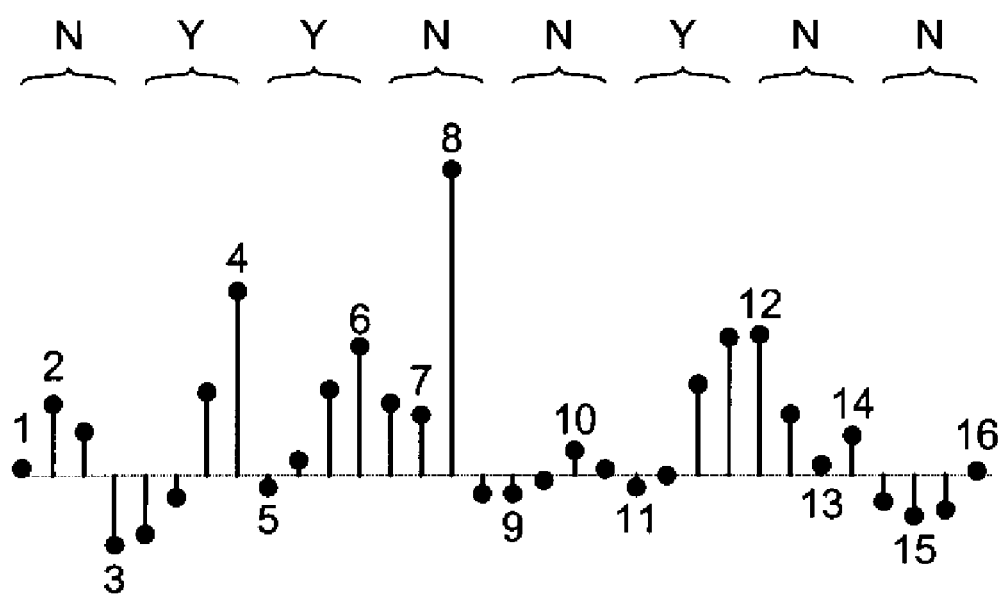

FIGS. 10A-10B show operation of an illustrative appraisal operation on a sensed event 120, however, in this example, the sensed event 120 is a low quality event that does not resemble a typical cardiac event. Again, FIG. 10A illustrates the sensed event 120 in continuous, analog form. FIG. 10B is a sampled (and, if desired, digitized), temporally ordered form of the event, and again indicates analytical results with numbers, brackets, and letters. Using the method of FIG. 7, the sensed event 120 includes sixteen monotonic segments. Again using the threshold of six, this sensed event 120 fails to meet the threshold and would be considered suspect. As a result, the method of FIG. 7 would not certify the sensed event 120.

Applying the method of FIG. 8, the sensed event 120 has four groups that are monotonic segments. Again, using a threshold of five monotonic segments to be certifiable, the sensed event 120 would be found suspect. Application of the method of FIG. 7 would, again, not certify the sensed event 120.

In another implementation, various techniques described herein may include a method of waveform appraisal that includes counting certain maximum slope points in a cardiac signal. The purpose of the maximum slope counter is to capture slope variation in the signal during the generated set of data. Low quality signals tend to have much more first derivative variation than a clean high quality cardiac signal. To capture the variation of the first derivative, the second derivative of the generated set is computed and checked for zero crossings. For an illustrative implementation, a zero crossing of the second derivative is defined as one where the second derivative crosses from a non-zero negative to a non-zero positive value and vice versa. Preferably, simply reaching zero is not considered a zero crossing point. Zero crossings of the second derivative of a single generally correspond to the points of local maximum slope (either positive or negative) of the original signal.

For the illustrative implementation, the first second derivative zero crossing is accepted as a significant maximum slope point. After that, as each maximum slope point is encountered, it is checked to see if it is significant by applying two rules based on path length. The path length is defined as an accumulation of the magnitude of amplitude changes in the original signal. The rules for the illustrative implementation are as follows:

1. The path length of the signal between the last significant maximum slope point and the current maximum slope point must be greater than the amplitude difference between the two points.

2. The path length of the signal between the last significant maximum slope point and the current maximum slope point must be greater than a programmed threshold value, derived as a percentage (50%) of the average peak amplitudes of the beats recorded prior to the current detection. If desired, a maximum or minimum for the threshold value may be set. In an illustrative example, using an 8 bit ADC, if the derived threshold value is less than 7 ADC units, the threshold is set at 7 ADC units. If the derived threshold value is greater than 20 ADC units, the threshold is set at 20 ADC units.

Figure 11:
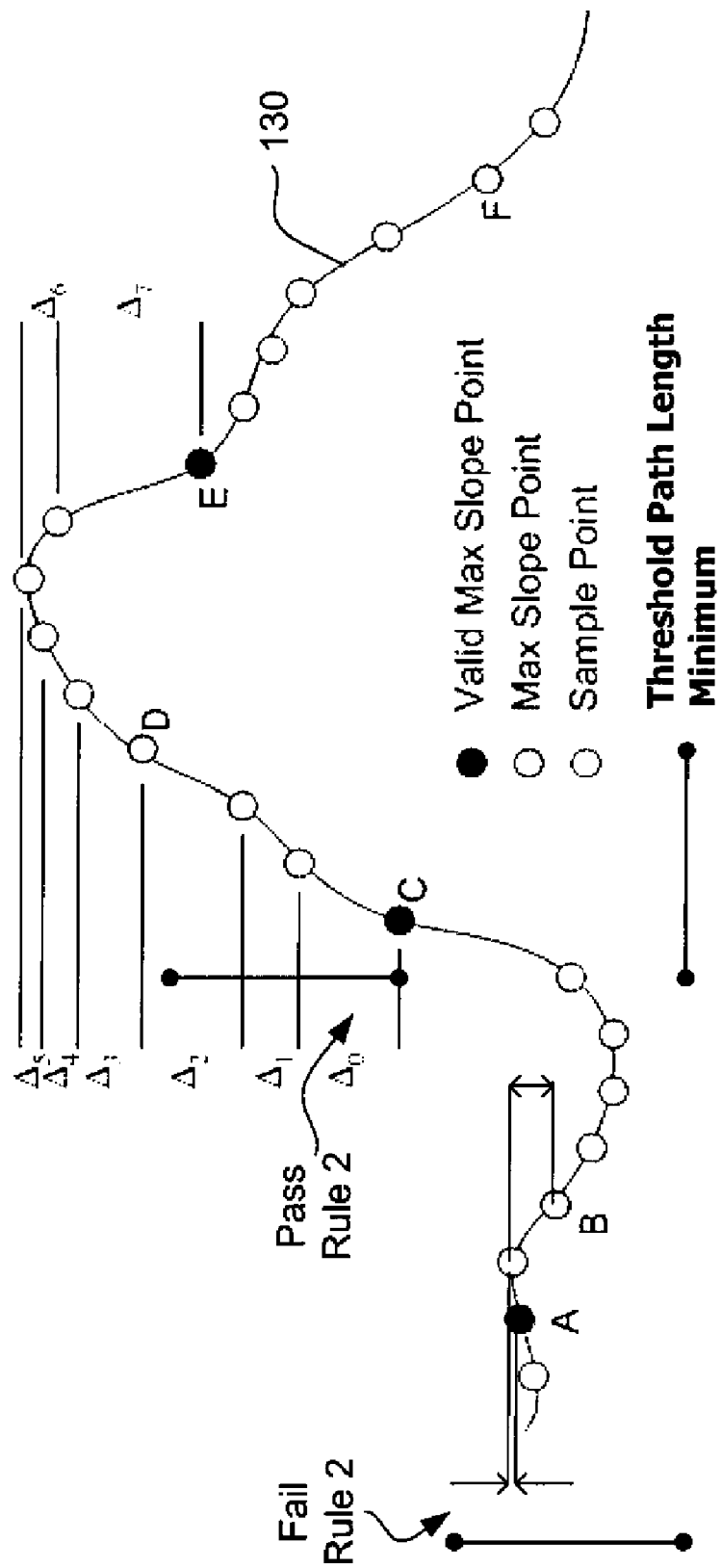
FIG. 11 illustrates, graphically, operation of another waveform appraisal method further illustrated in FIG. 12 in accordance with implementations of various technologies described herein.

FIG. 11 illustrates a method of signal analysis for counting significant maximum slope points. In the illustrative example, a number of signal sample points are shown along with a corresponding analog signal 130. The method includes determining where the second derivative of the sampled signal crosses zero, indicating a maximum magnitude for the slope of the signal at each point. Points A, B, C, D, E and F indicate these points.

Next, the method includes the step of determining which of points A-F are significant for the purpose of appraising the signal. The magnitude of amplitude change from point to point is determined, including the magnitude of such changes for the intermediate points between points A-F. These amplitude changes are indicated as segments Δ0-Δ7 in FIG. 11. A path length value is then determined. The path length value, as noted above, is the accumulation of the magnitude of amplitude changes in the sampled signal occurring between two points. Thus, the sum of the magnitudes of segments Δ0 to Δ2 is the path length from C to D, the sum of the magnitudes of segments Δ0 to Δ7 is the path length from C to E, and the sum of the magnitudes of segments Δ3 to Δ7 is the path length from D to E.

Next, the actual change in signal amplitude between the points is measured. With these values, the two rules noted above are applied to determine which maximum slope points are significant for appraising the signal. For illustrative purposes, point C is assumed to be certified (C would in fact be certified in the Figure). Using point C as a reference point, from point C to point D, the path length is the same as the amplitude change, therefore, point D is not a significant maximum slope point under Rule 1. Therefore, point D is rejected.

The next step is to go to the next identified maximum slope point, point E, to determine if it is significant for the appraisal method. In this case, the path length from point C to point E exceeds the amplitude change between these two points. Rule 2 is passed because the path length exceeds the illustrated threshold path length minimum. Because the requirements of both rules are met, point E is a significant maximum slope point for the appraisal method.

In further illustration, it can be seen that point B is not a significant maximum slope point because the path length from point A to point B does not exceed the threshold path length minimum. This fails Rule 1, above, and point B would be rejected.

The above analysis yields three significant maximum slope points in the signal shown in FIG. 11. If, for example, the threshold maximum number of significant maximum slope points is set at six, then the illustrated signal is considered a certified signal.

Figure 12:
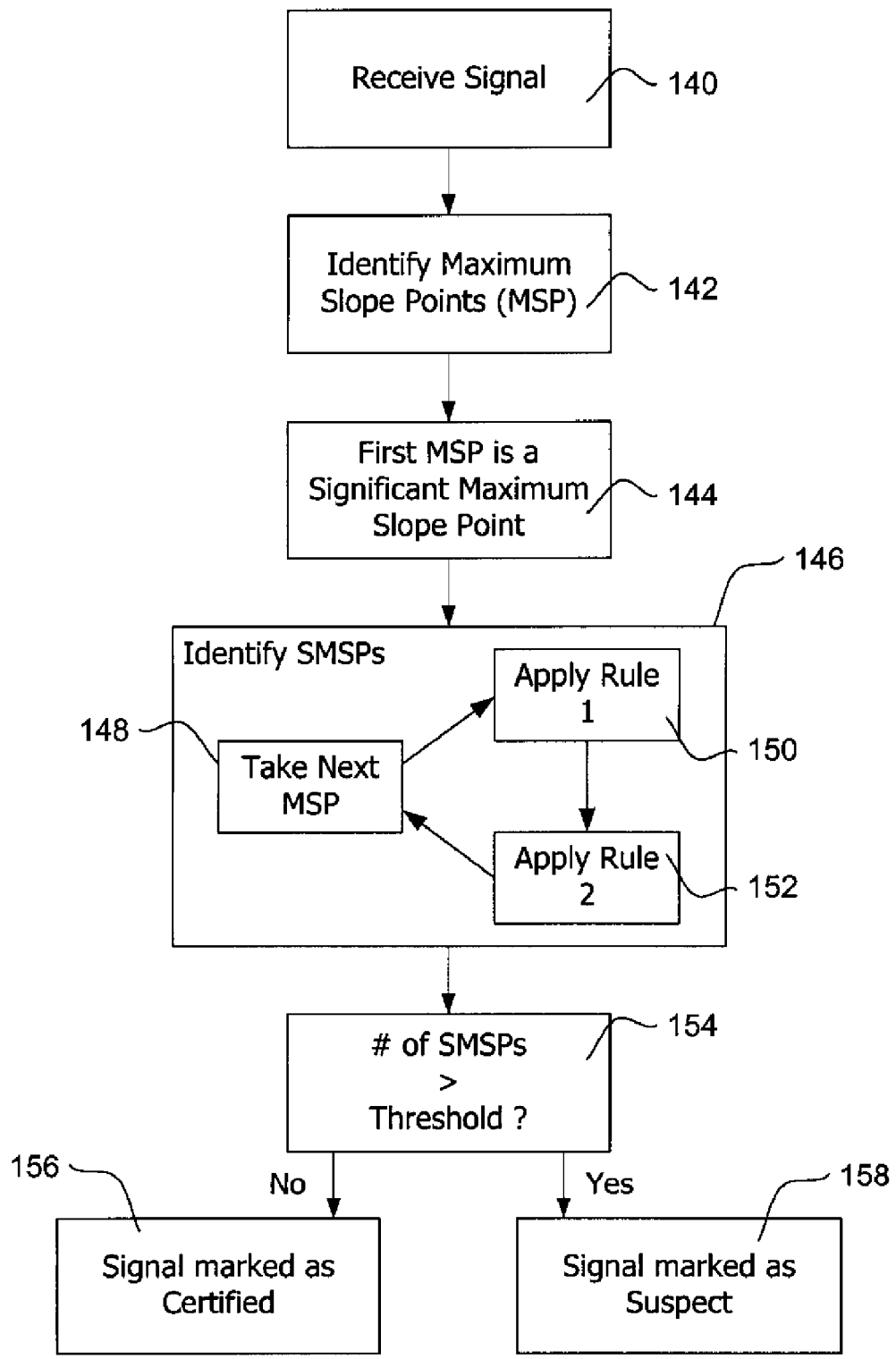
FIG. 12 shows a block diagram illustrating the steps employed in a maximum slope point method of waveform appraisal in accordance with implementations of various technologies described herein.

FIG. 12 shows in block form steps of an illustrative maximum slope point counting method for appraising a received signal. The method begins by receiving a signal, as shown at 140. Next, the maximum slope points are identified, as noted at 142. The first maximum slope point is identified as a significant maximum slope point, as noted at 144. As illustrated in block 146, the rest of the significant maximum slope points are identified by taking a next maximum slope point as shown at 148, and applying the first rule as shown at 150 and the second rule as shown at 152. After the significant maximum slope points are identified in block 148, the number of significant maximum slope points is compared to a threshold, as shown at 154. If the threshold is not exceeded, the signal is certified, as noted at 156. If the threshold is exceeded, then the signal is marked as suspect, as noted at 158. In some implementations, after the signal is marked as suspect, it may be subjected to further analysis, for example, to determine if changes in the event detection architecture are needed. In other implementations, suspect signals are discarded.

The following illustrative implementations are explained in terms of operational circuitry. The operational circuitry may be configured to include such controllers, microcontrollers, logic devices, memory, and the like, as selected, needed, or desired, for performing the steps for which each is configured.

An illustrative implementation includes an implantable cardioverter/defibrillator comprising a lead electrode assembly including a number of electrodes, and a canister housing operational circuitry. For the illustrative implementation, the lead electrode assembly is coupled to the canister; and the operational circuitry is configured to receive a cardiac signal from implanted electrodes, observe characteristic features of the shape of the signal, count the characteristic features, and compare the number of characteristic features to a threshold. With the comparison to the threshold, the operational circuitry is further configured to certify the signal for use in characterizing a cardiac complex, or determine the signal is unsuitable for use in characterizing a cardiac complex. In another implementation, the operational circuitry is configured such that the step of receiving a signal includes sensing electrical activity and using an event detector to determine the parameters of the signal. In yet a further implementation, the operational circuitry is configured such that the step of observing characteristic features includes identifying a number of points in the signal where the signal slope reaches a local maximum magnitude.

For a related illustrative implementation, the implantable cardioverter/defibrillator includes operational circuitry configured such that the step of identifying a number of points in the signal includes identifying zero crossings of the second derivative of the signal. In another implementation, the operational circuitry is configured such that the step of observing characteristic features includes selecting a first zero crossing as a significant maximum slope point, and characterizing subsequent zero crossings as either significant maximum slope points or not significant maximum slope points, wherein the significant maximum slope points are observed to be the characteristic features. In a related implementation, the operational circuitry is configured such that the step of characterizing subsequent zero crossings includes application of a rule related to a threshold for consideration of separate points in the signal. In yet another implementation, the operational circuitry is configured such that the rule calls for determining whether the path length from a most recent significant maximum slope point to the zero crossing under consideration exceeds a path length threshold. A further related implementation includes operational circuitry configured such that the path length threshold is related to a selected percentage of the maximum signal amplitude for a chosen cardiac complex.

In another implementation, the operational circuitry is configured such that the step of characterizing subsequent zero crossings includes application of a rule related to the signal shape between two points in the signal. In a further, related implementation, the operational circuitry is configured such that the rule calls for determining whether the path length from a most recent significant maximum slope point to the zero crossing under consideration exceeds the magnitude of the difference in amplitude between the signal at the time of the most recent significant maximum slope point, and the signal at the time of the zero crossing under consideration.

In another implementation, the operational circuitry is configured such that a step of characterizing subsequent zero crossings includes analysis using a first rule and a second rule, the first rule being related to a threshold for consideration of separate points in the signal, the second rule being related to the signal shape between two points in the signal. In a further implementation, the operational circuitry is configured such that the first rule calls for determining whether the path length from a most recent significant maximum slope point to the zero crossing under consideration exceeds a path length threshold, and the second rule calls for determining whether the path length from a most recent significant maximum slope point to the zero crossing under consideration exceeds the magnitude of the difference in amplitude between, the signal at the time of the most recent significant maximum slope point, and the signal at the time of the zero crossing under consideration. In another related implementation, the operational circuitry is configured such that the step of observing characteristic features of the signal includes assessment of the degree of monotonicity of the signal.

In another implementation, the operational circuitry is configured such that the step of observing characteristic features of the signal includes counting a number of monotonic segments of the signal. Yet another implementation includes operational circuitry configured such that the signal has a duration of less than one second. In several implementations, the implantable cardioverter/defibrillator includes operational circuitry comprising a controller and a controller readable memory.

An illustrative implementation includes an implantable cardioverter/defibrillator comprising a lead electrode assembly including a number of electrodes, and a canister housing operational circuitry, wherein the lead electrode assembly is coupled to the canister, and the operational circuitry is configured to: sample a signal from an implanted electrode; identify maximum slope points in the sample signal corresponding to local signal slope maximums; analyze the sample signal to determine which of the maximum slope points are significant; and compare the number of significant maximum slope points to a threshold.

Another illustrative implementation includes an implantable cardioverter/defibrillator comprising a lead electrode assembly including a number of electrodes, and a canister housing operational circuitry, wherein the lead electrode assembly is coupled to the canister, and the operational circuitry is configured to: receive a signal from a pair of implanted electrodes; sense whether a likely cardiac event has occurred; observe the monotonic characteristics of the signal during a time period corresponding to the likely cardiac event; and determine whether the signal during the time period is sufficiently monotonic to indicate the cardiac signal can be certified for classifying a cardiac rhythm. In a further implementation, the operational circuitry is configured such that the step of observing the monotonic characteristics includes grouping together samples of the cardiac signal from the time period into sample groups, and observing whether each sample group is monotonic. In yet another implementation, the operational circuitry is configured such that the step of observing the monotonic characteristics includes counting the number of times that an ordered set of samples of the cardiac signal corresponding to the time period changes its direction of amplitude change. Another illustrative implementation includes operational circuitry is configured such that the step of observing the monotonic characteristics includes counting a number of monotonic segments found in a sampling of the cardiac signal corresponding to the time period. An illustrative implementation further includes operational circuitry configured to classify the event to determine whether the event indicates treatment. In another implementation, the operational circuitry is further configured to determine whether a cardiac signal appears to indicate a patient's heart is beating at a rate above a rate threshold before performing the receive, sense, observe, and determine steps. In yet another implementation, the operational circuitry comprises a controller and a controller readable memory.

An illustrative implementation includes an implantable cardioverter/defibrillator comprising a lead electrode assembly including a number of electrodes, and a canister housing operational circuitry, wherein the lead electrode assembly is coupled to the canister, and the operational circuitry is configured to: sample a cardiac signal from a pair of implanted electrodes; define a number of groups of samples from a portion of the signal; determine how many of the groups of samples are monotonic; and, if the number of monotonic groups does not exceed a threshold, discard the portion of the signal.

Another illustrative implementation includes an implantable cardioverter/defibrillator comprising a lead electrode assembly including a number of electrodes, and a canister housing operational circuitry, wherein the lead electrode assembly is coupled to the canister, and the operational circuitry is configured to determine whether a heart is pumping at a rate exceeding a threshold, and, if so, perform the following steps: sample a cardiac signal from a pair of implanted electrodes; define a number of groups of samples from a portion of the signal; determine how many of the groups of samples are monotonic; and if the number of monotonic groups does not exceed a threshold, discard the portion of the signal. In another implementation, the operational circuitry is further configured to classify the signal by analyzing non-discarded portions of the signal, wherein the step of classifying the signal includes classifying portions of the signal as either indicating treatment or not indicating treatment. In yet another illustrative implementation, the operational circuitry is further configured such that the step of classifying the signal includes keeping a count of classified portions until a threshold number of portions are classified; wherein, when the threshold number of portions are classified, the method further includes determining whether to provide treatment based upon whether a predetermined number of classified portions indicate treatment.

Another illustrative implementation includes an implantable cardioverter/defibrillator comprising a lead electrode assembly including a number of electrodes, and a canister housing operational circuitry, wherein the lead electrode assembly is coupled to the canister, and the operational circuitry is configured to: sample a signal from first and second implanted electrodes; set a threshold for the monotonicity of a sensed signal; determine whether the sampled signal meets the threshold; and if the sampled signal does not meet the threshold, discard the signal.

Yet another illustrative implementation includes an implantable cardioverter/defibrillator comprising a lead electrode assembly including a number of electrodes, and a canister housing operational circuitry, wherein the lead electrode assembly is coupled to the canister, and the operational circuitry is configured to: receive a signal from first and second implanted electrodes; observe a point in the signal; observe a number of samples of the signal following the point; group the samples into a number of groups; observe which of the groups are monotonic; count the monotonic groups; determine whether the number of monotonic groups exceeds a threshold; and, if the number of monotonic groups does not exceed the threshold, discard the portion of the signal from which the number of signals following the point were taken.

An illustrative implementation includes an implantable cardioverter/defibrillator comprising a lead electrode assembly including a number of electrodes, and a canister housing operational circuitry, wherein the lead electrode assembly is coupled to the canister, and the operational circuitry is configured to: receive a signal from first and second implanted electrodes; observe a monotonic segment of the signal; measure the length of the monotonic segment; compare the length to a threshold; and, if the length is less than the threshold, determine that the monotonic segment does not correspond to a certifiable cardiac event. In a related implementation, the operational circuitry is further configured to observe a portion of the signal around the monotonic segment, determine whether the monotonic segment ends in a highest signal strength for the portion, and, if the monotonic segment does not end in a highest signal strength for the portion, determining that the monotonic segment does not correspond to a certifiable cardiac event. In another implementation, the operational circuitry is further configured such that the portion corresponds to time window around the monotonic segment, at least a portion of the time window occurring before the monotonic segment begins, and at least a portion of the time window occurring after the monotonic segment ends, the window having a duration in the range of 50-250 milliseconds.

Another implementation includes an implantable cardiac treatment system comprising first and second electrodes, and circuitry contained in a housing, the circuitry electrically coupled to the first and second electrodes, wherein the circuitry is adapted to perform the following steps: sampling a signal from first and second implanted electrodes; setting a threshold for the monotonicity of a sensed signal; determining whether the sampled signal meets the threshold; and, if the sampled signal does not meet the threshold, discarding the signal. In a further implementation, the circuitry includes a controller and a controller readable medium, the controller readable medium containing instructions thereon for performing the steps of sampling, setting, determining and discarding.

Yet another implementation includes an implantable cardioverter/defibrillator comprising a lead electrode assembly including a number of electrodes, and a canister housing operational circuitry, wherein the lead electrode assembly is coupled to the canister, and the operational circuitry is configured to monitor a signal produced between implanted electrodes to observe an event, observe an event and gathering a signal corresponding to the event, observe characteristic features of the shape of the signal, count the characteristic features, and compare the number of characteristic features to a threshold to certify the signal for use in characterizing a cardiac complex, or determine the signal is unsuitable for use in characterizing a cardiac complex. In the illustrative implementation, if the signal is certified, the operational circuitry is also configured to use the signal to determine whether a malignant cardiac rhythm is likely occurring.

An illustrative implementation includes an implantable cardioverter/defibrillator comprising a lead electrode assembly including a number of electrodes, and a canister housing operational circuitry, wherein the lead electrode assembly is coupled to the canister, and the operational circuitry is configured to capture a signal using implanted electrodes placed for observing electrical cardiac activity, analyze the signal to determine whether the signal is suitable for characterizing a cardiac rhythm, and, if the signal is suitable, use the signal to determine whether a malignant cardiac rhythm is likely occurring, or, if the signal is not suitable, reject the signal.

While the foregoing is directed to implementations of various technologies described herein, other and further implementations may be devised without departing from the basic scope thereof, which may be determined by the claims that follow. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method of monitoring cardiac function in an implantable cardiac rhythm device (ICRD), the ICRD comprising a plurality of electrodes adapted for implantation in a patient and operational circuitry electrically coupled to the electrodes and configured to perform analysis of cardiac signals, the method comprising:
   monitoring a signal produced between the electrodes;
   observing an event in the monitored signal;
   gathering a signal corresponding to and including the event in an analysis window;
   observing characteristic features of the slope of the signal in the analysis window;
   counting the characteristic features to determine the quantity of characteristic features that occur during the analysis window;
   comparing the quantity of characteristic features that occur in the signal during the analysis window to a threshold to:
      certify the event for use in characterizing a cardiac complex; or
      determine the event is unsuitable for use in characterizing a cardiac complex; and
   if the event is certified, using the event to determine whether a malignant cardiac arrhythmia is likely occurring; or
   if the event is not certified, excluding the event from analysis of whether a malignant cardiac arrhythmia is likely occurring.

2. The method of claim 1 wherein:
   the step of counting the characteristic features includes identifying an integer value equal to how many characteristic features there are in the signal; and
   the step of comparing the quantity of characteristic features to a threshold includes comparing the integer value to the threshold.

3. The method of claim 2 wherein the step of comparing the quantity of characteristic features to the threshold is performed as a single comparison of an integer value to the threshold for each observed event.

4. The method of claim 1, wherein the step of observing characteristic features includes identifying a number of points in the signal where the signal slope reaches a local maximum magnitude, representing zero crossings of the second derivative of the signal.

5. The method of claim 4, wherein the step of observing characteristic features includes:
   selecting a first zero crossing of the second derivative as a significant maximum slope point; and
   characterizing subsequent zero crossings of the second derivative as either significant maximum slope points or not significant maximum slope points;

wherein the significant maximum slope points are observed to be the characteristic features.

6. The method of claim 4, wherein comparing the quantity of characteristic features that occur during the analysis window to a threshold is performed by:
certifying the event for use in characterizing a cardiac complex if the quantity is less than the threshold; and
determining the event is unsuitable for use in characterizing a cardiac complex is the quantity is greater than the threshold.

7. The method of claim 5, wherein the step of characterizing subsequent zero crossings of the second derivative includes determining whether the path length from a most recent significant maximum slope point to the zero crossing of the second derivative under consideration exceeds a path length threshold, and:
if so, finding the zero crossing of the second derivative under consideration to be a significant maximum slope point;
if not, ignoring the zero crossing of the second derivative under consideration.

8. The method of claim 7, wherein the path length threshold is related to a selected percentage of the maximum signal amplitude for a chosen cardiac complex.

9. The method of claim 5, wherein the step of characterizing subsequent zero crossings of the second derivative includes application of a rule related to the signal shape between two points in the signal.

10. The method of claim 9, wherein the rule calls for determining whether the path length from a most recent significant maximum slope point to the zero crossing of the second derivative under consideration exceeds the magnitude of the difference in amplitude between:
the signal at the time of the most recent significant maximum slope point; and
the signal at the time of the zero crossing of the second derivative under consideration.

11. The method of claim 5, wherein the step of characterizing subsequent zero crossings of the second derivative includes analysis using a first rule and a second rule, wherein:
the first rule calls for determining whether the path length from a most recent significant maximum slope point to the zero crossing of the second derivative under consideration exceeds a path length threshold; and
the second rule calls for determining whether the path length from a most recent significant maximum slope point to the zero crossing of the second derivative under consideration exceeds the magnitude of the difference in amplitude between:
the signal at the time of the most recent significant maximum slope point; and
the signal at the time of the zero crossing of the second derivative under consideration.

12. The method of claim 1, wherein:
the step of observing characteristic features of the signal includes:
sampling the signal to generate a set samples; and
dividing the sampled signal into divisions each including a plurality of the samples;
the step of counting the characteristics features includes counting how many of the divisions are monotonic to yield a number M; and
the step of comparing the quantity of characteristic features to the threshold includes comparing M to the threshold.

13. A method of cardiac rhythm management using an implantable cardiac rhythm device (ICRD), the ICRD comprising a plurality of electrodes adapted for implantation in a patient and operational circuitry electrically coupled to the electrodes and configured to perform analysis of cardiac signals, the method comprising:
capturing a signal using the electrodes;
analyzing the signal to determine whether the signal is suitable for characterizing a cardiac rhythm;
if the signal is suitable, using the signal to determine whether a malignant cardiac arrhythmia is likely occurring; and
if the signal is not suitable, rejecting the signal;
wherein the step of analyzing the signal to determine whether the signal is suitable for characterizing a cardiac rhythm includes:
sampling the captured signal;
detecting an event in the captured, sampled signal;
selecting a number of samples including the detected event;
dividing the number of samples into a number of divisions each including plurality of samples;
counting how many of the number of divisions are monotonic to yield a number, M; and
comparing M to a threshold;
wherein if M is greater than the threshold, the signal is found to be suitable.

14. An implantable cardioverter/defibrillator (ICD) comprising:
a lead electrode assembly including a number of electrodes; and
a canister housing operational circuitry; wherein:
the lead electrode assembly is coupled to the canister; and
the operational circuitry is configured to:
monitor a signal produced between the electrodes;
observe an event in the monitored signal;
gather a signal corresponding to and including the event in an analysis window;
observe characteristic features of the shape of the signal in the analysis window;
count the characteristic features to determine the quantity of characteristic features that occur during the analysis window;
compare the quantity of characteristic features that occur in the signal during the analysis window to a threshold to:
certify the event for use in characterizing a cardiac complex; or
determine the event is unsuitable for use in characterizing a cardiac complex; and,
if the event is certified, use the event to determine whether a malignant cardiac arrhythmia is likely occurring; or
if the event is not certified, excluding the event from analysis of whether a malignant cardiac arrhythmia is likely occurring.

15. The ICD of claim 14 wherein the operational circuitry is configured such that:
the step of counting the characteristic features includes identifying an integer value equal to how many characteristic features there are in the signal; and
the step of comparing the quantity of characteristic features to a threshold includes comparing the integer value to the threshold.

16. The method of claim 15 wherein the operational circuitry is configured such that the step of comparing the quantity of characteristic features to the threshold is performed as a single comparison of an integer value to the threshold for each observed event.

17. The ICD of claim 14 wherein the operational circuitry is configured such that the step of observing characteristic features includes identifying a number of points in the signal where the signal slope reaches a local maximum magnitude, representing zero crossings of the second derivative of the signal.

18. The ICD of claim 17 wherein the operational circuitry is configured such that the step of observing characteristic features includes:
   selecting a first zero crossing of the second derivative as a significant maximum slope point; and
   characterizing subsequent zero crossings of the second derivative as either significant maximum slope points or not significant maximum slope points;
   wherein the significant maximum slope points are observed to be the characteristic features.

19. The ICD of claim 17, wherein the operational circuitry is configured such that the step of comparing the quantity of characteristic features that occur during the analysis window to a threshold is performed by:
   certifying the event for use in characterizing a cardiac complex if the quantity is less than the threshold; and
   determining the event is unsuitable for use in characterizing a cardiac complex is the quantity is greater than the threshold.

20. The ICD of claim 18 wherein the operational circuitry is configured such that the step of characterizing subsequent zero crossings of the second derivative includes analysis using a first rule and a second rule, wherein:
   the first rule calls for determining whether the path length from a most recent significant maximum slope point to the zero crossing of the second derivative under consideration exceeds a path length threshold; and
   the second rule calls for determining whether the path length from a most recent significant maximum slope point to the zero crossing of the second derivative under consideration exceeds the magnitude of the difference in amplitude between:
      the signal at the time of the most recent significant maximum slope point; and
      the signal at the time of the zero crossing of the second derivative under consideration.

21. The ICD of claim 18 wherein the operational circuitry is configured such that the step of characterizing subsequent zero crossings of the second derivative includes determining whether the path length from a most recent significant maximum slope point to the zero crossing of the second derivative under consideration exceeds a path length threshold; and
   if so, finding the zero crossing of the second derivative under consideration to be a significant maximum slope point;
   if not, ignoring the zero crossing of the second derivative under consideration.

22. The ICD of claim 21 wherein the operational circuitry is configured such that the path length threshold is related to a selected percentage of the maximum signal amplitude for a chosen cardiac complex.

23. The ICD of claim 18 wherein the operational circuitry is configured such that the step of characterizing subsequent zero crossings of the second derivative includes application of a rule related to the signal shape between two points in the signal.

24. The ICD of claim 23 wherein the operational circuitry is configured such that the rule calls for determining whether the path length from a most recent significant maximum slope point to the zero crossing of the second derivative under consideration exceeds the magnitude of the difference in amplitude between:
   the signal at the time of the most recent significant maximum slope point; and
   the signal at the time of the zero crossing of the second derivative under consideration.

25. The ICD of claim 14 wherein the operational circuitry is configured such that:
   the step of observing characteristic features of the signal includes:
      sampling the signal to generate a set samples; and
      dividing the sampled signal into divisions each including a plurality of the samples;
   the step of counting the characteristics features includes counting how many of the divisions are monotonic to yield a number M; and
   the step of comparing the quantity of characteristic features to the threshold includes comparing M to the threshold.

26. An implantable cardioverter/defibrillator (ICD) comprising:
   a lead electrode assembly including a number of electrodes; and
   a canister housing operational circuitry; wherein:
   the lead electrode assembly is coupled to the canister; and
   the operational circuitry is configured to:
   capture a signal using the electrodes;
   analyze the signal to determine whether the signal is suitable for characterizing a cardiac rhythm; and
   if the signal is suitable, use the signal to determine whether a malignant cardiac arrhythmia is likely occurring;
   if the signal is not suitable, reject the signal;
   wherein the operational circuitry is configured such that the step of analyzing the signal to determine whether the signal is suitable for characterizing a cardiac rhythm includes:
   dividing the captured signal into a number of samples, and dividing the number of samples into a number of time-contiguous divisions;
   counting how many of the number of divisions are monotonic to yield a number, M; and
   comparing M to a threshold;
   wherein if M is greater than the threshold, the signal is found to be suitable.

* * * * *